United States Patent
Fujii

(10) Patent No.: US 6,698,273 B2
(45) Date of Patent: Mar. 2, 2004

(54) METHOD AND APPARATUS FOR INSPECTING AIRTIGHTNESS OF GAS SENSOR

(75) Inventor: Kazuhiro Fujii, Mie-ken (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 10/135,428

(22) Filed: May 1, 2002

(65) Prior Publication Data

US 2002/0162382 A1 Nov. 7, 2002

(30) Foreign Application Priority Data

May 2, 2001 (JP) ........................................ 2001-135376

(51) Int. Cl.$^7$ ............................................... G01M 3/04
(52) U.S. Cl. .................................. 73/37; 73/40; 73/49.7
(58) Field of Search ............................... 73/37, 40, 49.7, 73/1.02, 1.06

(56) References Cited

U.S. PATENT DOCUMENTS

| | | | | |
|---|---|---|---|---|
| 5,212,979 A | * | 5/1993 | Albrodt et al. ................ | 73/37 |
| 5,228,975 A | * | 7/1993 | Yamada et al. .............. | 204/424 |
| 5,834,631 A | * | 11/1998 | Yamaguti et al. .............. | 73/40 |

FOREIGN PATENT DOCUMENTS

| | | | | |
|---|---|---|---|---|
| JP | 8-15076 | * | 1/1996 | ..................... 73/40 |
| JP | 8-43241 | * | 2/1996 | ..................... 73/40 |
| JP | 10-10082 | | 1/1998 | |
| JP | 10-260153 | * | 9/1998 | ................. 73/49.7 |

* cited by examiner

*Primary Examiner*—Daniel S. Larkin
(74) *Attorney, Agent, or Firm*—Nixon & Vanderhye P.C.

(57) ABSTRACT

An apparatus for inspecting the airtightness of a gas sensor includes an atmosphere-side jig located at a base end side of a sub assembly of the gas sensor, and a measurement gas-side jig located at a distal end side of the sub assembly. The measurement gas-side jig includes an air chamber, a socket receiving the sub assembly, and a high-pressure air source supplying a high-pressure air to the air chamber. The atmosphere-side jig includes a sealed chamber, a socket receiving the sub assembly, an airtight sealing portion, a low-pressure air source supplying the sealed chamber with a pressure lower than a pressure of the high-pressure air supplied to the air chamber, and a sensor portion leading to the sealed chamber.

5 Claims, 2 Drawing Sheets

METHOD AND APPARATUS FOR INSPECTING AIRTIGHTNESS OF GAS SENSOR

BACKGROUND OF THE INVENTION

1. Field of the Invention

This invention relates to a method and an apparatus for inspecting the airtightness of a gas sensor used in, for example, control of the burning of an air-fuel mixture in an internal combustion engine.

2. Description of the Related Art

Japanese patent application publication number 10-10082 discloses a gas sensor designed to enhance the degree of the sealing between a metal fitting body and a sensor element. In the gas sensor of Japanese application 10-10082, a sealant is provided between an inner circumferential surface of a body and an outer circumferential surface of the sensor element. The sealant is pressed by an insulating member. An annular spring is coaxially located between the insulating member and a flange of a cylinder. An edge of a rear end of the body is bent inward to cover the flange of the cylinder, and is axially deformed to compress the sealant. A rear end face of the insulating member presses an inner portion of a front end face of the annular spring along an axial direction while a front end face of the flange of the cylinder presses an outer portion of a rear end face of the annular spring in the axial direction. Thus, the annular spring is resiliently deformed, continuously urging the insulating member in the direction of compressing the sealant.

Another known gas sensor includes a sub assembly in which a gas sensor element having a reference gas chamber is disposed. The sub assembly has a base end side covered with an atmosphere-side cover surrounded by an atmosphere. The atmosphere-side cover defines an atmosphere chamber filled with the atmosphere. The gas sensor element is exposed to a measurement gas introduced into a measurement gas chamber extending in the sub assembly. The atmosphere is introduced into the reference gas chamber as a reference gas via, for example, holes provided through the walls of the atmosphere-side cover. The measurement gas chamber and the atmosphere chamber are airtightly isolated from each other. Therefore, the introduced measurement gas and the introduced atmosphere are airtightly separated from each other. The gas sensor element has a first electrode exposed to the measurement gas, and a second electrode exposed to the reference gas (the atmosphere). A specific-component concentration in the measurement gas is detected on the basis of an electrochemical reaction occurring between the first and second electrodes. During the manufacture of the known gas sensor, the airtightness of the isolation between the measurement gas chamber and the atmosphere chamber is inspected.

SUMMARY OF THE INVENTION

It is a first object of this invention to provide an improved apparatus for inspecting the airtightness of a gas sensor.

It is a second object of this invention to provide an improved method of inspecting the airtightness of a gas sensor.

A first aspect of this invention provides an apparatus for inspecting the airtightness of a gas sensor. The gas sensor includes a gas sensor element, a sub assembly, and an atmosphere-side cover, the gas sensor element having a reference gas chamber and being disposed in the sub assembly, the atmosphere-side cover covering a base end side of the sub assembly and defining an atmosphere chamber extending outward of the sub assembly, the sub assembly having a measurement gas chamber therein, the gas sensor element being exposed in the measurement gas chamber, the atmosphere chamber communicating with the reference gas chamber, the atmosphere chamber and the measurement gas chamber being airtight isolated from each other. The apparatus operates for inspecting the airtightness of the isolation between the atmosphere chamber and the measurement gas chamber. The apparatus comprises an atmosphere-side jig located at the base end side of the sub assembly; and a measurement gas-side jig located at a distal end side of the sub assembly; wherein the measurement gas-side jig includes (1) an air chamber into which the distal end side of the sub assembly extends and which communicates with the measurement gas chamber, (2) a first socket receiving the sub assembly whose distal end side extends into the air chamber, and (3) a high-pressure air source supplying a high-pressure air to the air chamber; and wherein the atmosphere-side jig includes (1) a sealed chamber into which the base end side of the sub assembly extends and which communicates with the atmosphere chamber, (2) a second socket receiving the sub assembly whose base end side extends into the sealed chamber, (3) an airtight sealing portion providing airtight contact between the second socket and the sub assembly, (4) a low-pressure air source supplying the sealed chamber with a pressure lower than a pressure of the high-pressure air supplied to the air chamber, and (5) a sensor portion leading to the sealed chamber.

A second aspect of this invention is based on the first aspect thereof, and provides an apparatus wherein the sensor portion includes a first pipe connected between the low-pressure air source and the sealed chamber, a first valve provided in the first pipe, a second pipe having a first end connected with the low-pressure air source and a second end being closed, a third pipe connected between the first pipe and the second pipe, and a diaphragm provided in the third pipe.

A third aspect of this invention provides a method of inspecting the airtightness of a gas sensor. The gas sensor includes a gas sensor element, a sub assembly, and an atmosphere-side cover, the gas sensor element having a reference gas chamber and being disposed in the sub assembly, the atmosphere-side cover covering a base end side of the sub assembly and defining an atmosphere chamber extending outward of the sub assembly, the sub assembly having a measurement gas chamber therein, the gas sensor element being exposed in the measurement gas chamber, the atmosphere chamber communicating with the reference gas chamber, the atmosphere chamber and the measurement gas chamber being isolated from each other in an airtight manner. The method is of inspecting the airtightness of the isolation between the atmosphere chamber and the measurement gas chamber. The method comprises the steps of supplying high-pressure air to a distal end side of the sub assembly to introduce the high-pressure air into the measurement gas chamber; applying a low pressure to the base end side of the sub assembly to supply the low pressure to the atmosphere chamber, the low pressure being lower than a pressure of the high-pressure air introduced into the measurement gas chamber; and monitoring a variation in a pressure in the atmosphere chamber to detect an air leakage from the measurement gas chamber into the atmosphere chamber.

A fourth aspect of this invention is based on the third aspect thereof, and provides a method wherein the step of supplying the high-pressure air follows the step of applying the low pressure.

A fifth aspect of this invention provides an apparatus for inspecting the airtightness of a gas sensor. The gas sensor includes a first chamber for containing a reference gas during actual use of the gas sensor, and a second chamber for containing a measurement gas during actual use of the gas sensor. The apparatus comprises first means for applying a predetermined pressure to the second chamber; and second means for monitoring a pressure in the first chamber to detect an air leakage from the second chamber into the first chamber when the first means applies the predetermined pressure to the second chamber.

A sixth aspect of this invention provides an apparatus for inspecting the airtightness of a gas sensor. The gas sensor includes a first chamber for containing a reference gas during actual use of the gas sensor, and a second chamber for containing a measurement gas during actual use of the gas sensor. The apparatus comprises a pressure source generating a first predetermined pressure; first means for connecting the first chamber with the pressure source to subject the first chamber to the first predetermined pressure; second means for disconnecting the first chamber from the pressure source after the first means connects the first chamber with the pressure source; third means for applying a second predetermined pressure higher than the first predetermined pressure to the second chamber; and fourth means for monitoring a difference between a pressure in the first chamber and the first predetermined pressure to detect an air leakage from the second chamber into the first chamber after the second means disconnects the first chamber from the pressure source and when the third means applies the second predetermined pressure to the second chamber.

DETAILED DESCRIPTION OF THE INVENTION

Basic Embodiment

Figure 1:
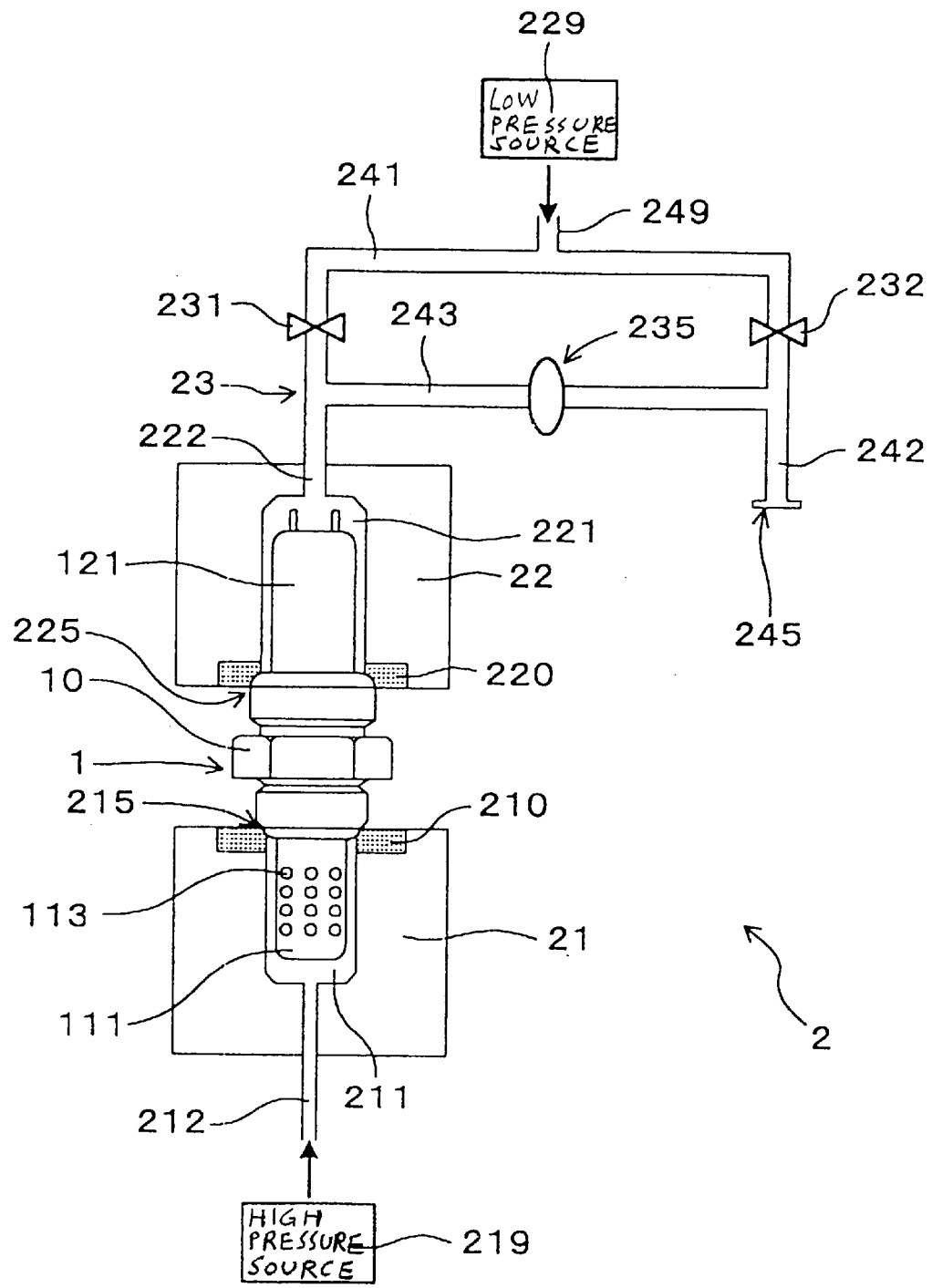
FIG. 1 is a diagram of an apparatus for inspecting the airtightness of a gas sensor according to a specific embodiment of this invention.

An apparatus in a basic embodiment of this invention is designed to inspect the airtightness of a gas sensor. A first example of the gas sensor includes a gas sensor element, a sub assembly, and an atmosphere-side cover. The gas sensor element has a reference gas chamber, and is disposed in the sub assembly. The atmosphere-side cover conceals a base end side of the sub assembly, and defines an atmosphere chamber extending outward of the sub assembly. The sub assembly has a measurement gas chamber therein. The gas sensor element is exposed in the measurement gas chamber. The atmosphere chamber communicates with the reference gas chamber. The atmosphere chamber and the measurement gas chamber are airtightly isolated from each other. The apparatus operates for inspecting the airtightness of the isolation between the atmosphere chamber and the measurement gas chamber.

The apparatus includes an atmosphere-side jig located at the base end side of the sub assembly, and a measurement gas-side jig located at a distal end side of the sub assembly. The measurement gas-side jig includes an air chamber into which the distal end side of the sub assembly extends and which communicates with the measurement gas chamber, a first socket receiving the sub assembly whose distal end side extends into the air chamber, and a high-pressure air source supplying a high-pressure air to the air chamber. The atmosphere-side jig includes a sealed chamber into which the base end side of the sub assembly extends and which communicates with the atmosphere chamber, a second socket receiving the sub assembly whose base end side extends into the sealed chamber, an airtight sealing portion providing airtight contact between the second socket and the sub assembly, a low-pressure air source supplying the sealed chamber with a pressure lower than a pressure of the high-pressure air supplied to the air chamber, and a sensor portion leading to the sealed chamber.

The airtight sealing portion is made of, for example, silicone rubber or urethane rubber. The airtight sealing portion has a good sealing performance. Preferably, the hardness of the airtight sealing portion is in the range of seventy to ninety. According to this hardness setting, the airtight sealing portion is excellent in abrasion and wear resistance. In the case where the hardness of the airtight sealing portion is lower than seventy, the airtight sealing portion tends to deteriorate at an early stage. In the case where the hardness of the airtight sealing portion exceeds ninety, there is a chance that a break in each of portions of the sub assembly fails to be found.

The airtight sealing member has a surface (a contact surface) in contact with the sub assembly. Preferably, the contact surface of the airtight sealing portion is shaped into conformity with a corresponding portion of the sub assembly. In this case, the airtight sealing portion contacts with the sub assembly in an airtight manner. Thus, the airtight sealing portion has a high sealing performance.

A second example of the gas sensor includes a cylindrical housing, and a gas sensor element inserted through the housing in an airtight manner. A measurement gas-side cover is provided on a distal end side of the housing to cover a distal end side of the gas sensor element. An atmosphere-side cover is provided on a base end side of the housing. The base end side of the gas sensor is exposed to an atmosphere while the distal end side thereof is exposed to a measurement gas. An airtight structure is provided between the gas sensor element and the housing so that the atmosphere and the measurement gas will be separated from each other.

A third example of the gas sensor is similar to the second example thereof except that an insulator is provided between the gas sensor element and the housing. A fourth example of the gas sensor is similar to the first, second, or third example thereof except that a heater is additionally provided.

The gas sensor element is of, for example, a cup-shaped type or a laminate type.

The sub assembly forms an inner potion of the gas sensor which includes the gas sensor element. The gas sensor element contacts with both a measurement gas and an atmosphere to detect a specific-component concentration in the measurement gas. The atmosphere is used as a reference gas. In the sub assembly, the measurement gas and the atmosphere are airtightly separated from each other. The atmosphere-side cover conceals the base end side of the sub assembly, and defines an atmosphere chamber filled with the atmosphere.

The high-pressure air supplied to the air chamber imitates the measurement gas fed to the gas sensor during actual use thereof. The pressure condition in the sealed chamber imitates the atmosphere fed to the gas sensor during actual use thereof.

Preferably, the sensor portion includes a first pipe connected between the low-pressure air source and the sealed chamber, a first valve provided in the first pipe, a second pipe having a first end connected with the low-pressure air source and a second end being closed, a third pipe connected between the first pipe and the second pipe, and a diaphragm provided in the third pipe. The diaphragm is sensitive to the difference between the pressure in the first pipe and the pressure in the second pipe. The diaphragm is used in detecting a pressure condition caused by an air leakage from the measurement gas chamber to the atmosphere chamber. The diaphragm can be offset by a pressure. According to the offset, a low pressure applied to the atmosphere side can be regarded as a zero pressure.

Specific Embodiment

Figure 2:
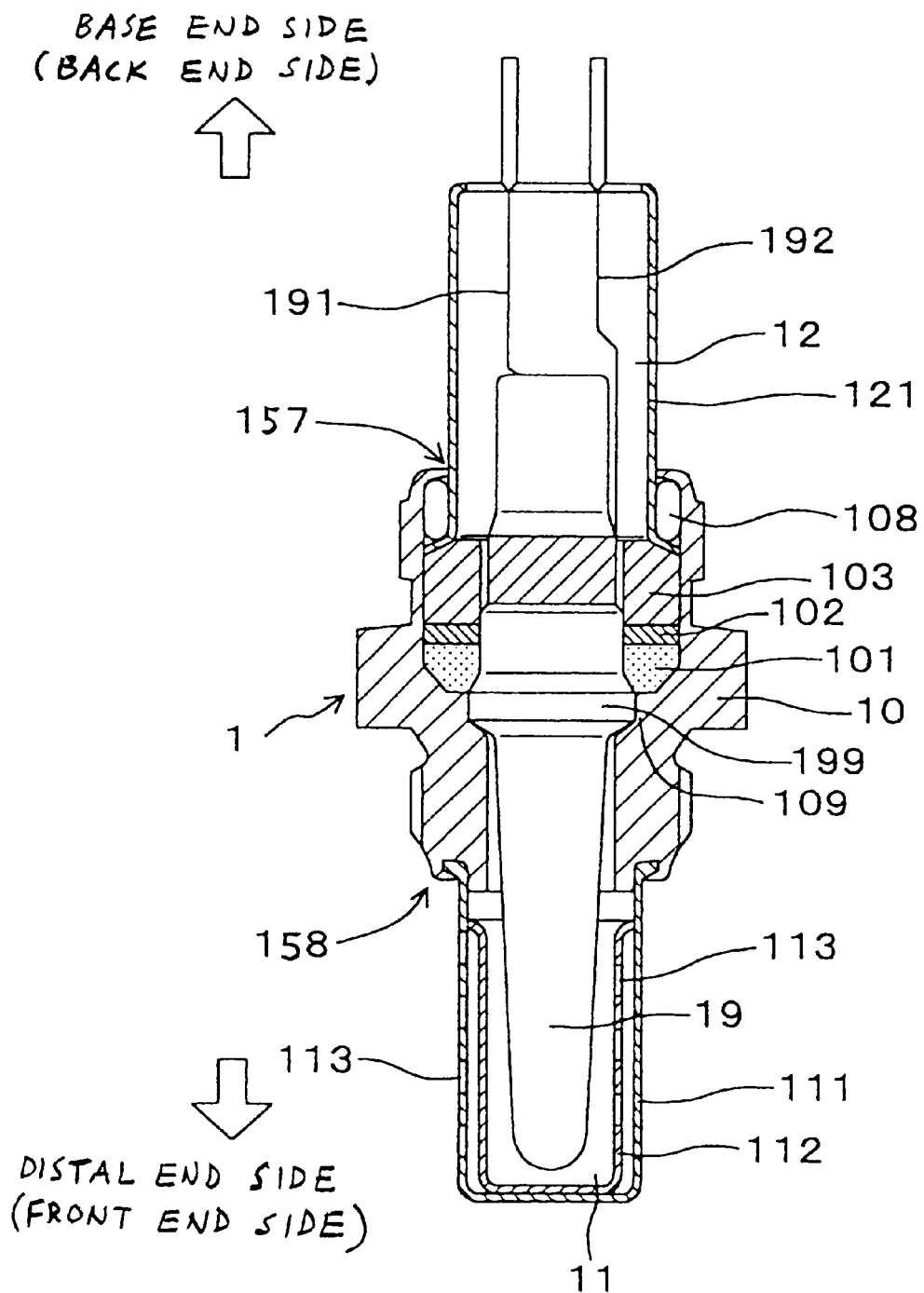
FIG. 2 is a longitudinal section view of a gas sensor in FIG. 1.

FIG. 1 shows an apparatus 2 for inspecting the airtightness of a gas sensor according to a specific embodiment of this invention. FIG. 2 shows the details of the gas sensor.

With reference to FIGS. 1 and 2, the gas sensor includes a sub assembly 1 in which a cup-shaped gas sensor element 19 having a reference gas chamber (not shown) is disposed. The sub assembly 1 has a base end side or a back end side covered with an outer atmosphere-side cover (not shown) surrounded by an atmosphere. The outer atmosphere-side cover defines a portion of a chamber (an atmosphere chamber) extending outward of the sub assembly 1 and filled with an atmosphere. An interior of the sub assembly 1 has a chamber 11 filled with a measurement gas to which the gas sensor element 19 is exposed. The chamber 11 is also referred to as the measurement gas chamber 11. The gas sensor element 19 is exposed in the measurement gas chamber 11. The atmosphere chamber communicates with the reference gas chamber so that the atmosphere can be introduced thereinto as a reference gas. The atmosphere chamber and the measurement gas chamber 11 are airtightly separated and isolated from each other.

The apparatus 2 is designed to inspect the airtightness of the separation and isolation between the atmosphere chamber and the measurement gas chamber 11 in the gas sensor. The apparatus 2 includes a measurement gas-side jig 21 and an atmosphere-side jig 22. The measurement gas-side jig 21 is located at a distal end side or a front end side of the sub assembly 1. The atmosphere-side jig 22 is located at the base end side of the sub assembly 1.

The measurement gas-side jig 21 has a member defining an air chamber 211. The measurement gas-side jig 21 further has a socket 215 and a high-pressure air source 219. The distal end side of the sub assembly 1 is placed into the air chamber 211. The sub assembly 1 is received by the socket 215 when the distal end side of the sub assembly 1 is placed into the air chamber 211. At that time, the air chamber 211 communicates with the measurement gas chamber 11 in the gas sensor. An end of the air chamber 211 is closed when the sub assembly 1 contacts with the socket 215. The high-pressure air source 219 supplies high-pressure air to the air chamber 211. In other words, the high-pressure air source 219 applies a high pressure to the air chamber 211.

The atmosphere-side jig 22 has a member defining a sealed chamber 221. The atmosphere-side jig 22 further has a socket 225, an airtightly sealing portion 220, a low-pressure air source 229, and a sensor portion 23. The base end side of the sub assembly 1 is placed into the sealed chamber 221. The sub assembly 1 is received by the socket 225 when the base end side of the sub assembly 1 is placed into the sealed chamber 221. At that time, the sealed chamber 221 communicates with the atmosphere chamber in the gas sensor. An inlet end of the sealed chamber 221 is closed when the sub assembly 1 contacts with the socket 225. The airtight sealing portion 220 provides airtight contact or airtight connection between the socket 225 and the sub assembly 1. The airtight sealing portion 220 defines the inlet end of the sealed chamber 221. When the sub assembly 1 contacts with the airtightly sealing portion 220, the inlet end of the sealed chamber 221 is closed. The low-pressure air source 229 supplies low-pressure air to the sealed chamber 221. In other words, the low-pressure air source 229 applies a low pressure to the sealed chamber 221. The pressure applied by the low-pressure air source 229 is lower than that applied by the high-pressure air source 219. The sensor portion 23 leads to the sealed chamber 221.

The sensor portion 23 includes a first pipe 241, a second pipe 242, and a third pipe 243. The first pipe 241 connects the low-pressure air source 229 and the sealed chamber 221. A first valve 231 is provided in the first pipe 241 to selectively block and unblock the first pipe 241. One end of the second pipe 242 is connected with the low-pressure air source 229 while the other end 245 thereof is closed. A second valve 232 is provided in the second pipe 242 to selectively block and unblock the second pipe 242. One end of the third pipe 243 is connected with a portion of the first pipe 241 between the first valve 231 and the sealed chamber 221. The other end of the third pipe 243 is connected with a portion of the second pipe 242 between the second valve 232 and the closed end thereof. A diaphragm 235 is provided in the third pipe 243. The diaphragm 235 divides the interior of the third pipe 243 into two portions. The diaphragm 235 deforms in accordance with the difference between the pressures applied to the opposite sides thereof. A strain gauge (not shown) is provided on the diaphragm 235. The strain gauge deforms as the diaphragm 235 deforms. The resistance of the strain gauge varies in accordance with deformation thereof. Thus, the resistance of the strain gauge depends on the difference between the pressures applied to the opposite sides of the diaphragm 235. An electrical circuit (not shown) connected with the strain gauge measures the resistance of the strain gauge to detect the difference between the pressures applied to the opposite sides of the diaphragm 235. The electric circuit may have a display for indicating the detected pressure difference.

The gas sensor is designed for use in an automotive internal combustion engine. Specifically, the gas sensor is located in an engine exhaust system, and is used in controlling the burning of an air-fuel mixture in the engine.

The gas sensor will be described below in more detail. The sub assembly 1 includes a cylindrical housing 10. The gas sensor element 19 airtightly extends through the cylindrical housing 10. The housing 10 has a front end side (a distal end side) provided with a measurement-gas-side cover of a double-wall structure which is composed of an outer cover 111 and an inner cover 112. A front end side or a distal end side of the gas sensor element 19 is covered with the inner and outer measurement-gas-side covers 111 and 112. The measurement gas chamber 11 is defined in the inner measurement-gas-side cover 112. The front end side of the gas sensor element 19 is located in the measurement gas chamber 11. The inner and outer measurement-gas-side covers 111 and 112 have a plurality of holes 113 for introducing a measurement gas, for example, an engine exhaust gas, into the measurement gas chamber 11. A base end side or a back end side of the housing 10 is covered with an inner atmosphere-side cover 121. A chamber 12 defined in the inner atmosphere-side cover 121 is a portion of the atmosphere chamber. Thus, the chamber 12 is filled with the atmosphere. The inner atmosphere-side cover 121 has holes for providing communication between the chamber 12 and a portion of the atmosphere chamber which extends outside the inner atmosphere-side cover 121.

The gas sensor element 19 has a cup-shaped solid electrolytic member made of zirconia. The solid electrolytic member can conduct oxygen ions. The reference gas chamber is defined in the solid electrolytic member. An outer electrode (not shown) is provided on an outer surface of the solid electrolytic member. The outer electrode is exposed to the measurement gas in the measurement gas chamber 11. An inner electrode (not shown) is provided on an inner surface of the solid electrolytic member. The inner electrode is exposed to the reference gas (the atmosphere) in the reference gas chamber.

A signal transmission lead and a terminal electrically connected with the outer electrode are formed on the outer surface of the solid electrolytic member. Also, a signal transmission lead and a terminal electrically connected with the inner electrode are formed on the inner surface of the solid electrolytic member. Connectors 191 and 192 for connection with the terminals are fixed to the body of the gas sensor element 19. External leads (not shown) are connected with the connectors 191 and 192 so that an electric signal can be transmitted from the gas sensor element 19 to an external device (not shown) placed outside the gas sensor.

An intermediate or central portion of the gas sensor element 19 has an annular flange-like projection 199 extending in radially outward directions. The inner surface portion of the housing 10 has an annular tapered portion 109. The projection 199 of the gas sensor element 19 is seated on the tapered portion 109 of the housing 10, and hence the gas sensor element 19 is supported by the housing 10.

An annular talc member 101, an annular metal packing 102, and an annular insulator 103 are sequentially placed on the projection 199 of the gas sensor element 19 and the tapered portion 109 of the housing 10. The talc member 101, the metal packing 102, and the insulator 103 extend between a portion of the outer surface of the gas sensor element 19 and a portion of the inner surface of the housing 10. The talc member 101, the metal packing 102, and the insulator 103 provide airtight connection between the gas sensor element 19 and the housing 10. The airtight connection between the gas sensor element 19 and the housing 10 causes airtight separation and isolation between the measurement gas and the atmosphere (the reference gas).

A fixing ring 108 is placed above the insulator 103. A lower edge of the inner atmosphere-side cover 121 is bent outward and an upper end of the housing 10 is bent inward so that the fixing ring 108 is firmly held therebetween. As a result, the inner atmosphere-side cover 121 is fixed to the housing 10 via the fixing ring 108. Thus, the fixation between the inner atmosphere-side cover 121 and the housing 10 is implemented by steps including a deforming and pressing step.

The apparatus 2 will be described below in more detail. The measurement gas-side jig 21 is basically made of dense metal. The socket 215 in the measurement gas-side jig 21 is a member on which a front end side 158 of the housing 10 of the sub assembly 1 is seated. The member of the socket 215 has a circular opening through which the sub assembly 1 extends. The socket 215 is formed with an airtight sealing portion 210 which provides airtight contact or airtight connection between the socket 215 and the sub assembly 1. The airtight sealing portion 210 defines an inlet end of the air chamber 211. When the front end side 158 of the housing 10 is seated on the airtight sealing portion 210, the inlet end of the air chamber 211 is closed. An air passage 212 connects the air chamber 211 and the high-pressure air source 219. High-pressure air is supplied to the air chamber 211 from the high-pressure air source 219 via the air passage 212.

The atmosphere-side jig 22 is basically made of dense metal. The socket 225 in the atmosphere-side jig 22 is a member on which a base end side (a back end side) 157 of the housing 10 of the sub assembly 1 is seated. The member of the socket 225 has a circular opening through which the sub assembly 1 extends. The socket 225 is formed with the airtightly sealing portion 220 which provides airtight contact or airtight connection between the socket 225 and the sub assembly 1. The airtight sealing portion 220 includes a sealing member made of silicone rubber or urethane rubber. The sealing member has a hardness preferably in the range of seventy to ninety. More preferably, the hardness is equal to 70. The sealing member has a surface (a contact surface) in contact with the housing 10. The contact surface of the sealing member has a shape conforming to the shape of a corresponding portion of the housing 10. Accordingly, the sealing member airtight contacts with the housing 10. The sealed chamber 221 leads to the sensor portion 23 via an air passage 222. The sensor portion 23 is interposed between the air passage 222 and the low-pressure air source 229. The low pressure can propagate from the low-pressure air source 229 to the sealed chamber 221 via the sensor portion 23 and the air passage 222.

The sensor portion 23 acts as a pressure difference sensor. The sensor portion 23 is designed to detect the difference in pressure between the low-pressure air source 229 and the sealed chamber 221. The sensor portion 23 includes a pipe 249 connected with the low-pressure air source 229. The pipe 249 branches into the first pipe 241 and the second pipe 242. The first valve 231 is provided in the first pipe 241 to selectively block and unblock the first pipe 241. The second valve 232 is provided in the second pipe 242 to selectively block and unblock the second pipe 242. The first pipe 241 leads to the air passage 222. The end of the second pipe 242 which is remote from the pipe 249 is closed. One end of the third pipe 243 is connected with a portion of the first pipe 241 between the first valve 231 and the air passage 222. The other end of the third pipe 243 is connected with a portion of the second pipe 242 between the second valve 232 and the closed end thereof. As previously mentioned, the diaphragm 235 is provided in the third pipe 243. The diaphragm 235 divides the interior of the third pipe 243 into two portions. The diaphragm 235 deforms in accordance with the difference between the pressures applied to the opposite sides thereof. The strain gauge is provided on the diaphragm 235. The strain gauge deforms as the diaphragm 235 deforms. The resistance of the strain gauge varies in accordance with deformation thereof. Thus, the resistance of the strain gauge depends on the difference between the pressures applied to the opposite sides of the diaphragm 235. As previously mentioned, the electrical circuit connected with the strain gauge measures the resistance of the strain gauge to detect the difference between the pressures applied to the opposite sides of the diaphragm 235. The electrical circuit may have a display for indicating the detected pressure difference.

During operation of the apparatus 2, the gas sensor is placed in position with respect to the measurement gas-side jig 21 and the atmosphere-side jig 22. The first valve 231 and the second valve 232 are opened. Air is drawn from the sealed chamber 221 toward the low-pressure air source 229 through the first valve 231. Also, air is drawn from the air passage 222, the first pipe 241, the second pipe 242, and the third pipe 243 toward the low-pressure air source 229. As a result, the pressures in the sealed chamber 221, the air passage 222, the first pipe 241, the second pipe 242, and the third pipe 243 are equalized to the pressure of the low-pressure air source 229. Then, the first valve 231 and the second valve 232 are closed. After the second valve 232 is closed, the pressure applied to the right-hand side (as viewed in FIG. 1) of the diaphragm 235 continues to be equal to the pressure of the low-pressure air source 229. The pressure of the low-pressure air source 229 is equal to 49.6.+−.1.9 kPa. The time for which the first and second valves 231 and 232 remain opened, that is, the time for which the low-pressure air source 229 continues to effectively operate on the sealed chamber 221 and the sensor portion 23, is equal to two seconds. The pressures in the sealed chamber 221, the air passage 222, the first pipe 241, the second pipe 242, and the third pipe 243 are equalized to the pressure of the low-pressure air source 229 within one second thereafter.

Subsequently, the high-pressure air source 219 supplies high-pressure air to the air chamber 211 via the air passage 212. The pressure of air supplied from the high-pressure air source 219 to the air chamber 211 is equal to 442±49 kPa. In cases where the airtightness of the sub assembly 1 is sufficient to prevent the occurrence of an air leakage from the air chamber 211 to the sealed chamber 221 through the sub assembly 1, the pressure in the sealed chamber 221 remains equal to the normal low level (the pressure of the low-pressure air source 229). In these cases, the pressure applied to the left-hand side (as viewed in FIG. 1) of the diaphragm 235 also remains equal to the normal low level. As a result, the pressure applied to the right-hand side of the diaphragm 235 and the pressure applied to the left-hand side thereof continue to be the same. The resistance of the strain gauge provided on the diaphragm 235 reflects the absence of a difference between the pressure applied to the right-hand side of the diaphragm 235 and the pressure applied to the left-hand side thereof. Therefore, the sufficient airtightness of the sub assembly 1 is detected by the electrical circuit connected with the strain gauge. The airtightness of the sub assembly 1 means that of isolation between the atmosphere chamber and the measurement gas chamber in the sub assembly 1. The previously-indicated air leakage from the air chamber 211 to the sealed chamber 221 through the sub assembly 1 means an air leakage from the measurement gas chamber 11 to the atmosphere chamber in the sub assembly 1. In the event that the airtightness of the sub assembly 1 is insufficient and hence air leaks from the air chamber 211 to the sealed chamber 221 through the sub assembly 1, the pressure in the sealed chamber 221 rises from the normal low level (the pressure of the low-pressure air source 229). Since the third pipe 243 extending leftward of the diaphragm 235 communicates with the sealed chamber 221 via the first pipe 241 and the air passage 222, the pressure rise propagates from the sealed chamber 221 to the left-hand side (as viewed in FIG. 1) of the diaphragm 235. As a result, there occurs a difference between the pressure applied to the right-hand side of the diaphragm 235 and the pressure applied to the left-hand side thereof. The resistance of the strain gauge provided on the diaphragm 235 varies in accordance with the difference between the pressure applied to the right-hand side of the diaphragm 235 and the pressure applied to the left-hand side thereof. Therefore, the pressure rise propagating from the sealed chamber 221 to the diaphragm 235 is detected by the electrical circuit connected with the strain gauge. Accordingly, the insufficient airtightness of the sub assembly 1 or the presence of an air leakage therethrough is detected by the electrical circuit.

After the pressure in the sealed chamber 221 is equalized to the pressure of the low-pressure air source 229 and before the high-pressure air source 219 supplies high-pressure air to the air chamber 211, the airtightness of the airtight sealing portion 220 is inspected. In the event that the airtightness of the airtight sealing portion 220 is insufficient, air is drawn into the sealed chamber 221 from an exterior through the contact between the airtight sealing portion 220 and the sub assembly 1. In this case, the pressure in the sealed chamber 221 rises from the normal low level (the pressure of the low-pressure air source 229). The pressure rise propagates from the sealed chamber 221 to the left-hand side of the diaphragm 235. As a result, there occurs a difference between the pressure applied to the right-hand side of the diaphragm 235 and the pressure applied to the left-hand side thereof. The resistance of the strain gauge provided on the diaphragm 235 varies in accordance with the difference between the pressure applied to the right-hand side of the diaphragm 235 and the pressure applied to the left-hand side thereof. Therefore, the pressure rise propagating from the sealed chamber 221 to the diaphragm 235 is detected by the electrical circuit connected with the strain gauge. Accordingly, the insufficient airtightness of the airtight sealing portion 220 is detected by the electrical circuit. The insufficient airtightness of the airtight sealing portion 220 is notified to an operator via the electrical circuit. When the insufficient airtightness of the airtight sealing portion 220 is detected, the airtight sealing portion 220 is replaced by new one. The interval for mandatory replacement of the airtight sealing portion 220 corresponds to a hundred thousand of times of the inspection of the gas sensor airtightness.

The apparatus 2 has the following advantages. The apparatus 2 can accurately inspect the airtightness of the gas sensor. The inspection of the gas sensor airtightness is executed in conditions close to conditions of actual use of the gas sensor.

What is claimed is:

1. An apparatus for inspecting the airtightness of a gas sensor including a gas sensor element, a sub assembly, and an atmosphere-side cover, the gas sensor element having a reference gas chamber and being disposed in the sub assembly, the atmosphere-side cover covering a base end side of the sub assembly and defining an atmosphere chamber extending outward of the sub assembly, the sub assembly having a measurement gas chamber therein, the gas sensor element being exposed in the measurement gas chamber, the atmosphere chamber communicating with the reference gas chamber, the atmosphere chamber and the measurement gas chamber being airtightly isolated from each other, the apparatus operating for inspecting the airtightness of the isolation between the atmosphere chamber and the measurement gas chamber, the apparatus comprising:

an atmosphere-side jig located at the base end side of the sub assembly; and a measurement gas-side located at a distal end side of the sub assembly;

wherein the measurement gas-side jig includes (1) an air chamber into which the distal end side of the sub assembly extends and which communicates with the measurement gas chamber, (2) a first socket receiving the sub assembly whose distal end side extends into the air chamber, and (3) a high-pressure air source supplying a high-pressure air to the air chamber; and wherein the atmosphere-side jig includes (1) a sealed chamber into which the base end side of the sub assembly extends and which communicates with the atmosphere chamber, (2) a second socket receiving the sub assembly whose base end side extends into the sealed chamber, (3) an airtight sealing portion providing airtight contact between the second socket and the sub assembly, (4) a low-pressure air source supplying the sealed chamber with a pressure lower than a pressure of the high-pressure air supplied to the air chamber, and (5) a sensor portion leading to the sealed chamber.

2. An apparatus as recited in claim 1, wherein the sensor portion includes a first pipe connected between the low-pressure air source and the sealed chamber, a first valve provided in the first pipe, a second pipe having a first end connected with the low-pressure air source and a second end being closed, a third pipe connected between the first pipe and the second pipe, and a diaphragm provided in the third pipe.

3. A method of inspecting the airtightness of a gas sensor including a gas sensor element, a sub assembly, and an atmosphere-side cover, the gas sensor element having a reference gas chamber and being disposed in the sub assembly, the atmosphere-side cover covering a base end side of the sub assembly and defining an atmosphere chamber extending outward of the sub assembly, the sub assembly having a measurement gas chamber therein, the gas sensor element being exposed in the measurement gas chamber, the atmosphere chamber communicating with the reference gas chamber, the atmosphere chamber and the measurement gas chamber being airtightly isolated from each other, the method being of inspecting the airtightness of the isolation between the atmosphere chamber and the measurement gas chamber, the method comprising:

supplying high-pressure air to a distal end side of the sub assembly to introduce the high-pressure air into the measurement gas chamber;

applying a low pressure to the base end side of the sub assembly to supply the low pressure to the atmosphere chamber, the low pressure being lower than a pressure of the high-pressure air introduced into the measurement gas chamber; and monitoring a variation in a pressure in the atmosphere chamber to detect an air leakage from the measurement gas chamber into the atmosphere chamber.

4. A method as recited in claim 3, wherein supplying the high-pressure air follows applying the low pressure.

5. An apparatus for inspecting the airtightness of a gas sensor including a first chamber for containing a reference gas during actual use of the gas sensor, and a second chamber for containing a measurement gas during actual use of the gas sensor, the apparatus comprising:

a pressure source generating a first predetermined pressure;

first means for connecting the first chamber with the pressure source to subject the first chamber to the first predetermined pressure;

second means for disconnecting the first chamber from the pressure source after the first means connects the first chamber with the pressure source;

third means for applying a second predetermined pressure higher than the first predetermined pressure to the second chamber; and fourth means for monitoring a difference between a pressure in the first chamber and the first predetermined pressure to detect an air leakage from the second chamber into the first chamber after the second means disconnects the first chamber from the pressure source and when the third means applies the second predetermined pressure to the second chamber.

* * * * *